(12) United States Patent
McBroom et al.

(10) Patent No.: US 7,951,999 B1
(45) Date of Patent: May 31, 2011

(54) SOYBEAN CULTIVAR S07-02JR409106

(75) Inventors: Roger McBroom, St Joseph, IL (US); Julia Brown, Sidell, IL (US)

(73) Assignee: Syngerta Participations AG, Basel (CH)

( * ) Notice: Subject to any disclaimer, the term of this patent is extended or adjusted under 35 U.S.C. 154(b) by 533 days.

(21) Appl. No.: 12/072,594

(22) Filed: Feb. 27, 2008

Related U.S. Application Data

(60) Provisional application No. 60/903,675, filed on Feb. 27, 2007.

(51) Int. Cl.
*A01H 5/00* (2006.01)
*C12N 15/82* (2006.01)

(52) U.S. Cl. .......... 800/312; 800/260; 435/415
(58) Field of Classification Search .......... None
See application file for complete search history.

(56) References Cited

U.S. PATENT DOCUMENTS

| | | | |
|---|---|---|---|
| 6,750,383 B2 | 6/2004 | McBroom et al. | |
| 7,453,029 B2 * | 11/2008 | Eby | 800/312 |

\* cited by examiner

*Primary Examiner* — Elizabeth F McElwain
(74) *Attorney, Agent, or Firm* — Dana Rewoldt

(57) ABSTRACT

The present invention is in the field of soybean cultivar S07-02JR409106 breeding and development. The present invention particularly relates to the soybean cultivar S07-02JR409106 and its progeny, and methods of making S07-02JR409106.

20 Claims, 2 Drawing Sheets

SOYBEAN CULTIVAR S07-02JR409106

REFERENCE TO RELATED APPLICATION

This application claims the benefit under Title 35, United States Code, §119(e) of U.S. provisional application 60/903,675 filed Feb. 27, 2007.

THE FIELD OF THE INVENTION

The present invention is in the field of soybean cultivar breeding and development. The present invention particularly relates to the soybean cultivar S07-02JR409106 and its progeny, and methods of making.

BACKGROUND OF THE INVENTION

Soybean *Glycine max* (L) is an important oil seed crop and a valuable field crop. However, it began as a wild plant. This plant and a number of other plants have been developed into valuable agricultural crops through years of breeding and development. The pace of the development of soybeans, into an animal foodstuff and as an oil seed has dramatically increased in the last one hundred years. Planned programs of soybean breeding have increased the growth, yield and environmental hardiness of the soybean germplasm.

Due to the sexual reproduction traits of the soybean, the plant is basically self-pollinating. A self-pollinating plant permits pollen from one flower to be transferred to the same or another flower of the same plant. Cross-pollination occurs when the flower is pollinated with pollen from a different plant; however, soybean cross-pollination is a rare occurrence in nature.

Thus the growth and development of new soybean germplasm requires intervention by the breeder into the pollination of the soybean. The breeders' methods of intervening in the pollination depend on the type of trait that is being bred. Soybeans are developed for a number of different types of traits morphological (form and structure), phenotypical, or for traits like growth, day length, temperature requirements, initiation date of floral or reproductive development, fatty acid content, insect resistance, disease resistance, nematode resistance, fungal resistance, herbicide resistance, tolerance to various environmental factors like drought, heat, wet, cold, wind, adverse soil condition and also for yield. The genetic complexity of the trait often drives the selection of the breeding method.

Due to the number of genes within each chromosome, millions of genetic combinations exist in the breeders' experimental soybean material. This genetic diversity is so vast that a breeder cannot produce the same two cultivars twice using the exact same starting parental material. Thus, developing a single variety of useful commercial soybean germplasm is highly unpredictable, and requires intensive research and development.

The development of new soybeans comes through breeding techniques, such as: recurrent selection, mass selections, backcrossing, single seed descent and multiple seed procedure. Additionally, marker assisted breeding allows more accurate movement of desired alleles or even specific genes or sections of chromosomes to be moved within the germplasm that the breeder is developing. RFLP, RAPD, AFLP, SSR, SNP, SCAR, isozymes, are some of the forms of markers that can be employed in breeding soybeans or in moving traits into soybean germplasm. Other breeding methods are known and are described in various plant breeding or soybean textbooks.

When a soybean variety is being employed to develop a new soybean variety or an improved variety the selection methods may include backcrossing, pedigree breeding, recurrent selection, marker assisted selection, modified selection and mass selection or a combination of these methods. The efficiency of the breeding procedure along with the goal of the breeding are the factors for determining which selection techniques are employed. A breeder continuously evaluates the success of the breeding program and therefore the efficiency of any breeding procedures. The success is usually measured by yield increase, commercial appeal and environmental adaptability of the developed germplasm.

The development of new soybean cultivars most often requires the development of hybrid crosses (some exceptions being initial development of mutants directly through the use of the mutating agent, certain materials introgressed by markers, or transformants made directly through transformation methods) and the selection of progeny. Hybrids can be achieved by manual manipulation of the sexual organs of the soybean or by the use of male sterility systems. Breeders often try to identify true hybrids by a readily identifiable trait or the visual differences between inbred and hybrid material. These heterozygous hybrids are then selected and repeatedly selfed and reselected to form new homozygous soybean lines.

Mass and recurrent selection can be used to improve populations. Several parents are intercrossed and plants are selected based on selected characteristics like superior yield or excellent progeny resistance. Outcrossing to a number of different parents creates fairly heterozygous breeding populations.

Pedigree breeding is commonly used with two parents that possess favorable, complementary traits. The parents are crossed to form a F1 hybrid. The progeny of the F1 hybrid is selected and the best individual F2s are selected; this selection process is repeated in the F3 and F4 generations. The inbreeding is carried forward and at approximately F5-F7 the best lines are selected and tested in the development stage for potential usefulness in a selected geographic area.

In backcross breeding a genetic allele or loci is often transferred into a desirable homozygous recurrent parent. The trait from the donor parent is tracked into the recurrent parent. The resultant plant is bred to be like the recurrent parent with the new desired allele or loci.

The single-seed descent method involves use of a segregating plant population for harvest of one seed per plant. Each seed sample is planted and the next generation is formed. When the F2 lines are advanced to approximately F6 or so, each plant will be derived from a different F2. The population will decline due to failure of some seeds, so not all F2 plants will be represented in the progeny.

New varieties must be tested thoroughly to compare their development with commercially available soybeans. This testing usually requires at least two years and up to six years of comparisons with other commercial soybeans. Varieties that lack the entire desirable package of traits can be used as parents in new populations for further selection or are simply discarded. The breeding and associated testing process is 8 to 12 years' of work prior to development of a new variety. Thousands of varietal lines are produced but only a few lines are selected in each step of the process. Thus the breeding system is like a funnel with numerous lines and selections in the first few years and fewer and fewer lines in the middle years until one line is selected for the final development testing.

The selected line or variety will be evaluated for its growth, development and yield. These traits of a soybean are a result of the variety's genetic potential interacting with its environment. All varieties have a maximum yield potential that is predetermined by its genetics. This hypothetical potential for yield is only obtained when the environmental conditions are near perfect. Since perfect growth conditions do not exist, field experimentation is necessary to provide the environmental influence and to measure its effect on the development and yield of the soybean. The breeder attempts to select for an elevated soybean yield potential under a number of different environmental conditions.

Selecting for good soybean yield potential in different environmental conditions is a process that requires planning based on the analysis of data in a number of seasons. Identification of the varieties carrying a superior combination of traits, which will give consistent yield potential, is a complex science. The desirable genotypic traits in the variety can often be masked by other plant traits, unusual weather patterns, diseases, and insect damage. One widely employed method of identifying a superior plant with such genotypic traits is to observe its performance relative to commercial and experimental plants in replicated studies. These types of studies give more certainty to the genetic potential and usefulness of the plant across a number of environments.

In summary, the goal of the soybean plant breeder is to produce new and unique soybeans and progeny of the soybeans for farmers' commercial crop production. To accomplish this, the plant breeder painstakingly crosses two or more varieties or germplasm. Then the results of this cross are repeatedly selfed or backcrossed to produce new genetic patterns. Newer avenues for producing new and unique genetic alleles in soybeans include introducing (or creating) mutations or transgenes into the genetic material of the soybean are now in practice in the breeding industry. These genetic alleles can alter pest resistance such as disease resistance, insect resistance, nematode resistance, herbicide resistance, or they can alter the plant's environmental tolerances, or its seeds fatty acid compositions, the amount of oil produced, and/or the amino acid/protein compositions of the soybean plant or its seed.

The traits a breeder selects for when developing new soybeans are driven by the ultimate goal of the end user of the product. Thus if the goal of the end user is to resist a certain plant disease so overall more yield is achieved, then the breeder drives the introduction of genetic alleles and their selection based on disease resistant levels shown by the plant. On the other hand, if the goal is to produce specific fatty acid composition, with for example a high level of oleic acid and/or a lower level of linolenic acid, then the breeder may drive the selection of genetic alleles/genes based on inclusion of mutations or transgenes that alter the levels of fatty acids in the seed. Reaching this goal may allow for the acceptance of some lesser yield potential or other less desirable agronomic trait.

The new genetic alleles being introduced in to soybeans are widening the potential uses and markets for the various products and by-products of the oil from the seed plants such as soybean. A major product extracted from soybeans is the oil in the seed. Soybean oil is employed in a number of retail products such as cooking oil, baked goods, margarines and the like. Another useful product is soybean meal, which is a component of many foods and animal feedstuffs.

SUMMARY OF THE INVENTION

One embodiment of the invention relates to seed of a soybean cultivar designated S07-02JR409106. The invention relates to the plant from the seed designated S07-02JR409106, or the plant parts. The invention also encompasses a tissue culture of regenerable cells, cells or protoplasts being from a tissue selected from the group consisting of: leaves, pollen, embryos, meristematic cells, roots, root tips, anthers, flowers, ovule, seeds, stems, pods, petals and the cells thereof.

The invention in one aspect covers a soybean plant, or parts thereof, having all of the physiological and morphological characteristics of the soybean plant.

Another aspect of this invention is the soybean plant seed or derived progeny which contains a transgene which provides herbicide resistance, insect resistance, resistance to disease, resistance to nematodes, male sterility, or which alters the oil profiles, the fatty acid profiles, the amino acids profiles or other nutritional qualities of the seed.

The present invention further covers a method for producing a soybean seed with the steps of crossing at least two parent soybean plants and harvesting the hybrid soybean seed, wherein at least one parent soybean plant is the present invention. Another aspect of the invention covers the hybrid soybean seed and the progeny soybean plant and its resultant seed, or parts thereof from the hybrid seed or plant or its progeny.

In an additional aspect, the invention covers a method for producing a soybean progeny from the invention by crossing soybean line S07-02JR409106 with a second soybean plant to yield progeny soybean seed and then growing progeny soybean seed to develop a derived soybean line.

Yet another aspect of the invention covers a method for a breeding program using plant breeding techniques which employ the soybean plant S07-02JR409106 as plant breeding material and performing breeding by selection techniques, backcrossing, pedigree breeding, marker enhanced selection, mutation and transformation.

DETAILED DESCRIPTION

Figure 1:
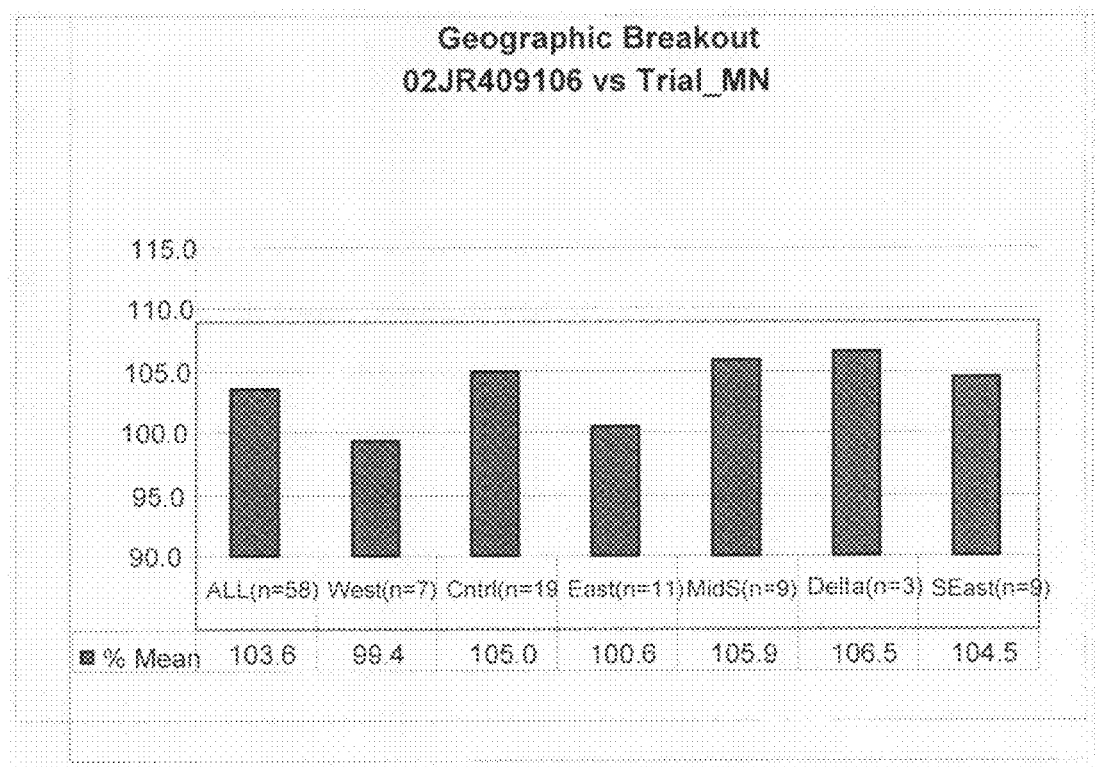
FIG. 1 shows the Geographic Segment Chart—GSEGC shows the breakout for grain yield at standard moisture for S07-02JR409106 across geographic locations.

The following data is used to describe and enable the present syoybean invention.

| TRAIT ABBREVIATIONS | TRAIT NAME | DESCRIPTION |
| --- | --- | --- |
| RRG_T | MC RR Gene Present RRG_T | Glyphosate Resistant Gene Present (Yes or No) |
| STS_T | MC Sulfonylurea Tolerant Soybean F | Sulfonylurea Tolerant Soybean (Yes or No) |
| FL_CT | MC Flower Color FL_CT | Flower Color - P = Purple, W = White or Segregating = Mixture of colors |

-continued

| TRAIT ABBREVIATIONS | TRAIT NAME | DESCRIPTION |
|---|---|---|
| PB_CT | MC Pubescence Color PB_CT | Pubescence Color - G = Gray, T = Tawny, Lt = Light Tawny, Segregating = Mixture of Colors |
| PD_CT | MC Pod Color PD_CT | Pod Color - T = Tawny, B = Brown, Segregating = Mix of Colors |
| HILCT | Hilum Color HILCT | Hilum Color - G = Gray, BR = Brown, BF = Buff, BL = Black, IB = Imperfect Black, Y = Yellow, IY = Imperfect Yellow, Segregating = Mixture of Colors |
| PRTNP | Protein Percent PRTNP | Protein Percent @ 13% Moisture |
| OIL_P | Oil Percent OIL_P | Oil Percent @ 13% Moisture |
| SBSSN | Seed Size (Number of Seeds per LB) SBSSN | Seed Size (Number of Seeds per pound) |
| STMTR | Stem Termination STMTR | Stem Termination 1 = Determinate 2 = Indeterminate 3 = Semi-Determinate 9 = Segregation |
| RPS_T | PRR GENE RPS_T | *Phytophthora* Root Rot GENE, 1C, 1K, No Gene, etc. |
| CN1_P | SCN Race 1 Female Index % | SCN Race 1 Female Index % |
| CN3_P | SCN Race 3 Female Index % | SCN Race 3 Female Index % |
| CN5_P | SCN Race 5 Female Index % | SCN Race 5 Female Index % |
| CN14P | SCN Race 14 Female Index % | SCN Race 14 Female Index % |
| SN_T | MC SCN Resistance source SN_T | Soybean Nematode Resistance Source |
| MI_R | Root Knot *Incognita* MI_R | Root Knot *Incognita* 1-9 (1 = best) |
| MA_R | Root Knot *Arenaria* MA_R | Root Knot *Arenaria* 1-9 (1 = best) |
| DPM_R | Stem Canker (Southern) DPM_R | Stem Canker (Southern) Rating 1-9 (1 = best) |
| DPMTR | Stem Canker (South) Tolerance DPMTR | Stem Canker (Southern) Tolerance Rating 1-9 (1 = best) |
| CLS_T | Chloride Sensitivity | Chloride Sensitivity Text Excluder = Accumulates Chloride and restricts the Chloride in the roots, Includer = Accumulates Chloride throughout the plant |
| VHNO | Variety/Hybrid Number | A code designating a particular variety |
| YGSMN | Grain Yield at Std MST - YGSMN | Grain Yield at Standard Moisture |
| MRTYN | Maturity Days from planting MRTYN | Maturity - Number of days from planting date until the cultivar has reached its maturity. |
| HLDGR | Harvest Lodging HLDGR | Harvest Lodging 1 = All erect; 5 = 45 degrees; 9 = flat |
| PLHTN | Plant Height (cm) | Plant Height in centimeters |
| GLDGR | Green Lodging GLDGR | Green Lodging Rating R5 to R6 1 = All erect, 5 = 45 degree, 9 = flat |
| PLCNR | Plant Canopy Rating PLCNR | Plant Canopy Rating 1 = No branching, 5 = Average, 9 = Profuse |
| PLBRR | Plant Branching PLBRR | Plant Branching Rating 1 = No branching, 5 = Average, 9 = Profuse |
| PRR_R | *Phytophthora* Root Rot Tolerance PRR_R | *Phytophthora* Root Rot Field Tolerance Rating 1-9 (1 = best) for field tolerance |
| BSR_R | Brown Stem Rot BSR_R | Brown Stem Rot Rating 1-9 (1 = best) |
| EMRGR | Emergence EMRGR | Emergence 1-9 (1 = best) |
| EPA_R | Early Plot Appearance EPA_R | Early Plot Appearance - emergence, evenness of stand V2-V6 |
| FELSR | Frogeye Leaf Spot FELSR | Frogeye Leaf Spot Rating 1-9 (1 = best) |
| GMSTP | Moisture % (Field) MST_P | Moisture % (Field) |
| GS_R | Green Stem GS_R | Green Stem Rating 1-9 (1 = best) |
| HVAPR | Harvest Appearance HVAPR | Overall Harvest Appearance 1 = Excellent; 5 = Average; 9 = Poor |
| IC_R | Iron Chlorosis IC_R | Iron Chlorosis Rating or Calculated from Flash & Recovery Mean 1-9 (1 = best) |
| ICFLR | Iron Chlorosis Yellow Flash Rate ICFLR | Iron Chlorosis Yellow Flash Rating 1-9 (1 = best) |
| ICR_R | Iron Chlorosis Recovery ICR_R | Iron Chlorosis Recovery Rating 1-9 (1 = best) |
| SDS_R | Sudden Death Syndrome SDS_R | Sudden Death Syndrome Rating 1-9 (1 = best) |
| STR_R | Shattering STR_R | Shattering 1-9 (1 = best) |
| TESTP | Test % TESTP | The Mean Yield of the variety, expressed as a percentage of the Mean Yield of all varieties in the trial. |

Trait Definitions

Hypocotyl Length (Hyp_R) A rating of a variety's hypocotyl extension after germination when planted at a 5" depth in sand and maintained in a warm germination environment for 10 days.

Seedling Establishment (EMRGR) A rating of uniform establishment and growth of seedlings.

Seed Coat Peroxidase (Perox)—seed protein peroxidase activity is a chemical taxonomic technique to separate cultivars based on the presence or absence of the peroxidase enzyme in the seed coat. Ratings are POS=positive for peroxidase enzyme or NEG=negative for peroxidase enzyme.

Plant Height (PLHTN) The average measured plant height in centimeters.

Plant Branching (PLBRR) Rating of the number of branches and their relative importance to yield. This rating is taken at growth expressive locations. 1=no branching, 5=average and 9=profuse.

Green Lodging (GLDGR) Rating based on the average of plants leaning from vertical in R5 to R6 stage prior to maturity. 1=all are erect, 5=average erectness. 9=all are flat. Rating one is the best rating.

Harvest Lodging (HLDGR) Rating based on the average of plants leaning from vertical at harvest. Lodging score (1=completely upright, 5=45 degree angle from upright; 9=completely prostrate). Rating one is the best rating.

*Phytophthora* Root Rot (PRR_R) means a *Phytophthora* Root Rot field tolerance rating. Rating is 1-9 with one being the best. The information can also include the listing of the actual resistance gene (RPS_T), for example, Rps gene 1C.

Root Knot Nematode (RKN) Greenhouse screen—45 day screen root inoculated with eggs and juveniles. Rating Scale based upon female reproduction index on a susceptible check set determined by number of galls present. Rating scale is 1-9 with 1 being best. Species specific ratings: Arenaria (MA_R), Incognita (MI_R), Javanica (MJ_R).

Stem Canker (DPM_R) Based on number of lesions, 1-9 rating. One being the best.

Brown Stem Rot (BSR_R) This disease is caused by the fungus *Phialophora gregata*. The disease is a late-season, cool-temperature, soil borne fungus which in appropriate favorable weather can cause up to 30 percent yield losses in soybean fields. BSR_R is an opportunistic field rating. The scale is 1-9. One rating is best.

Sudden Death Syndrome (SDS_R) This disease is caused by slow-growing strains of *Fursarium solani* that produce bluish pigments in culture. The disease is a mid to late season, soil borne disease that occurs in soybean fields. Yield losses may be total or severe in infected fields. The Sudden Death Syndrome Rating is an opportunistic field rating based on leaf area affected. The scale used for these tests is 1-9. A one rating is best.

*Sclerotinia* White Mold (SCL_R) This disease is caused by the fungal pathogen *Sclerotinia sclerotium*. The fungus can overwinter in the soil for many years as sclerotia and infect plants in prolonged periods of high humidity or rainfall. Yield losses may be total or severe in infected fields. *Sclerotinia* White Mold (SCL_R) rating is a field rating (1-9 scale) based on the percentage of wilting or dead plants in a plot. A one rating is best.

Frog Eye Leaf Spot (FELSR) This is caused by the fungal pathogen *Cercospora sojina*. The fungus survives as mycelium in infected seeds and in infested debris. With adequate moisture new leaves become infected as they develop until all the leaves are infected. Yield losses may be up to 15% in severe infected fields. Frog Eye Leaf Spot (FELSR) rating is a field rating (1-9 scale) based on the percentage of leaf area affected. The scale is 1-9 where 1=no leaf symptoms and 9=severe leaf symptoms. One is the best rating. To test varieties for Frog Eye Leaf Spot a disease nursery is artificially inoculated with spores. The ratings are done when the plants have reached the R5-R6 growth stage. Visual calibration is done with leaf photos of different frogeye severity ratings as used by the University of Tennessee and Dr. Melvin Newman, State Plant Pathologist for TN.

Soybean Cyst Nematode (SCN) The Soybean Cyst Nematode *Heterodera glycines*, is a small plant-parasitic roundworm that attacks the roots of soybeans. Soybean Cyst Nematode Ratings are taken from a 30 day greenhouse screen using infested soil. The rating scale is based upon Female Reproduction Index (FI %) on a susceptible check set where <10%=R (RESISTANT); >10%-<30%=MR (MODERATELY RESISTANT); >30%-<60%=MS (MODERATELY SUSPECTIBLE); >60%=S (SUSPECTIBLE). The screening races include: 1, 3, 5, 14. Individual ratings CN1—P, CN3—P, CN5—P, and CN14—P refer to the resistance to SCN races 1, 3, 5 and 14 FI % respectively.

Maturity Days from Planting (MRTYN) Plants are considered mature when 95% of the pods have reached their mature color. MRTYN is the number of days calculated from the number of days from planting date to 95% mature color.

Relative Maturity Group (RM) Industry Standard for varieties groups, based day length or latitude. Long day length (northern areas in the Northern Hemisphere) are classified as (Groups 000, 00, 0). Mid day lengths variety groups lie in the middle group (Groups I-VI). Very short day lengths variety groups (southern areas in Northern Hemisphere) are classified as (Groups VII, VIII, IX).

Grain Yield at Standard Moisture (YGSMN) The actual grain yield at standard moisture reported in the unit's bushels/acre.

Shattering (STR_R) The rate of pod dehiscence prior to harvest. Pod dehiscence is the process of beans dropping out of the pods. Advanced varieties are planted in a replicated nursery south of their adapted zone to promote early senescence. Mature plots are allowed to stand in the field to endure heat/cool and especially wet/dry cycles. Rating is based on the differences between varieties of the amount of open pods and soybeans that have fallen on the ground. The rating scale is 1-9 with 1=no shattering and 9=severe shattering. One rating is best.

Yield Test Percentage (TESTP) The mean yield of the subject variety expressed as a percentage of the mean yield of all varieties in the trial.

Plant Parts Means the embryos, anthers, pollen, nodes, roots, root tips, flowers, petals, pistols, seeds, pods, leaves, stems, meristematic cells and other cells (but only to the extent the genetic makeup of the cell has both paternal and maternal material) and the like.

Palmitic Acid Means a fatty acid, $C_{15}H_{31}COOH$, occurring in soybean. This is one of the five principal fatty acids of soybean oil.

Linolenic Acid Means an unsaturated fatty acid, $C_{17}H_{29}COOH$, occurring in soybean. This is one of the five principal fatty acids of soybean oil.

Stearic Acid Means a colorless, odorless, waxlike fatty acid, $CH_3(CH_2)_{16}COOH$, occurring in soybean. This is one of the five principal fatty acids of soybean oil.

Oleic Acid Means an oily liquid fatty acid, $C_{17}H_{33}COOH$, occurring in soybean. This is one of the five principal fatty acids of soybean oil.

Linoleic Acid Means an unsaturated fatty acid, $C_{17}H_{31}COOH$, occurring in soybean. This is one of the five principal fatty acids of soybean oil.

Plant Means the plant, in any of its stages of life including the seed or the embryo, the cotyledon, the plantlet, the immature or the mature plant, the plant parts, plant protoplasts, plant cells of tissue culture from which soybean plants can be regenerated, plant calli, plant clumps, and plant cells (but only to the extent the genetic makeup of the cell has both paternal and maternal material) that are intact in plants or parts of the plants, such as pollen, anther, nodes, roots, flowers, seeds, pods, leaves, stems, petals and the like.

Bud Blight (virus—tobacco ringspot virus): A virus disease of soybeans, symptoms form a curled brown crook out of the terminal bud of plants.

Soybean Mosaic (virus): This soybean virus appears as a yellow vein on infected plants. This virus will show in the veins of developing leaves. Leaves look narrow and have puckered margins. Infection results in less seed formed in odd shaped pods. The virus is vectored by aphids.

Bean Pod Mottle Virus (virus): The bean leaf beetle vectored virus. This virus causes a yellow-green mottling of the leaf particularly in cool weather.

Target Spot (fungus—*Alternaria* sp.): This fungus infects leaves, also shows spots on pods and stems.

Anthracnose (fungus—*Colletotrichum* dematium var. *truncatum*): This fungus infects stems, petioles and pods of almost mature plants.

Brown Leaf Spot (fungus—*Septoria glycines*): Early foliar disease on soybeans in springtime.

Downy Mildew (fungus—*Peronospora manshurica*): Fungus appears on the topside of the leaf. The fungus appears as indefinite yellowish-green areas on the leaf.

Purple Seed Stain (fungus—*Cercospora kikuchii*): This fungus is on the mature soybean seed coat and appears as a pink or light to dark purple discoloration.

Seed Decay and Seedling Diseases (fungi—*Pythium* sp., *Phytophthora* sp., *Rhizoctonia* sp., *Diaporthe* sp.): When damage or pathology causes reduced seed quality, then the soybean seedlings are often predisposed to these disease organisms.

Bacterial Blight (bacterium—*Pseudomonas syringae* pv. *glycinea*): A soybean disease that appears on young soybean plants.

Charcoal Rot (fungus—*Macrophomina phaseolina*): Charcoal rot is a sandy soil, mid-summer soybean disease.

*Rhizobium*-Induced Chlorosis: A chlorosis appearing as light green to white which appears 6-8 weeks during rapid plant growth.

Bacterial Pustule (bacterium—*Xanthomonas campestris* pv. *phaseoli*): This is usually a soybean leaf disease; however, the disease from the leaves may infect pods.

Cotton Root Rot (fungus—*Phymatotrichum omnivorum*): This summertime fungus causes plants to die suddenly.

Pod and Stem Blight (fungus—*Diaporthe phaseolorum* var. *sojae*): The fungus attacks the maturing pod and stem and kills the plant.

Treated Seed means the seed of the present invention with a pesticidal composition. Pesticidal compositions include but are not limited to material that are insecticidal, fungicidal, detrimental to pathogens, or sometimes herbicidal.

Definitions of Staging of Development

The plant development staging system employed in the testing of this invention divides stages as vegetative (V) and reproductive (R). This system accurately identifies the stages of any soybean plant. However, all plants in a given field will not be in the stage at the same time. Therefore, each specific V or R stage is defined as existing when 50% or more of the plants in the field are in or beyond that stage.

The first two stages of V are designated a VE (emergence) and VC (cotyledon stage). Subdivisions of the V stages are then designated numerically as V1, V2, V3 through V (n). The last V stage is designated as V (n), where (n) represents the number for the last node stage of the specific variety. The (n) will vary with variety and environment. The eight subdivisions of the reproductive stages (R) states are also designated numerically. R1=beginning bloom; R2=full bloom; R3=beginning pod; R4=full pod; R5=beginning seed; R6=full seed; R7=beginning maturity; R8=full maturity.

Soybean Cultivar S07-02JR409106

The invention is a novel soybean cultivar designated 02JR409106 with high yield potential, tolerance to Roundup™ herbicide, early Group 4 maturity, and resistance to races 3 and 14 of Soybean Cyst Nematode. The invention relates to seeds of the cultivars 02JR409106, plants of the cultivars 02JR409106, and to methods for producing a soybean plant produced by crossing the soybean 02JR409106 by itself or another soybean genotype.

The present invention S07-02JR409106 is be sold commercially in the central Midwest and Mid-south where other early to mid Maturity Group IV soybeans are grown, especially where there is infestation by Soybean Cyst Nematode.

The present invention was produced by crossing the parental lines, planting the resulting seeds, and then selfing and advancing the resulting plants using modified single seed descent to the F6 generation. Single plants were then harvested and threshed individually, and the resulting seeds were then planted in a replicated yield trial.

The present invention comprises a soybean plant characterized by molecular and physiological data obtained from the representative sample of said variety deposited with the American Type Culture Collection (ATCC). Additionally, the present invention comprises a soybean plant comprising the homozygous alleles of the variety, formed by the combination of the disclosed soybean plant or plant cell with another soybean plant or cell.

This soybean variety in one embodiment carries one or more transgenes, for example, the glyphosate tolerance transgene, a desaturase gene or other transgenes. In another embodiment of the invention, the soybean does not carry any herbicide resistance traits. In yet another embodiment of the invention, the soybean does not carry any transgenes but carries alleles for aphid resistance, cyst nematode resistance and/or brown stem rot or the like. In still another embodiment, the soybean carries both alleles and transgenes providing desired traits.

The traits of the invention are listed below.

| TRAITS | |
|---|---|
| Plant Characteristics | |
| Roundup Ready ® | Y |
| STS ® | N |
| Flower Color | White |
| Pubescence Color | Light Tawny |
| Pod Color | Brown |
| Hilum Color | Black |
| % Protein 13% mst. | 35.5 |
| % Oil @ 13% mst. | 16.9 |
| Seed Size/Lb | 3140 |
| Stem Termination | INDET |
| Plant Health | |
| Rps Gene | 1c |
| SCN RACE 1 FI % | |
| SCN RACE 3 FI % | 4.0 |
| SCN RACE 5 FI % | |
| SCN RACE 14 FI % | 0.0 |
| SCN Source | PI88788 |
| Root Knot Nematode - Incognita | |
| Root Knot Nematode - Arenaria | |
| Stem Canker (Southern) | 1.0 |
| Stem Canker Tolerance (Southern) | |
| Choride Sensitivity | Excluder |

Rps gene indicates the specific gene for resistance but if none are indicated then none are known to be present
Y = Yes, has trait.
N = No does not contain trait
SCN = Soybean Cyst Nematode
RoundUp Ready ®, Roundup ® and Roundup ® Ultra are trademarks of Monsanto Company.
STS ® is a trademark of DuPont.
Ratings are on a 1 to 9 scale with 1 being the best.

Additional Traits

| Descriptive Traits | | Performance Traits | |
|---|---|---|---|
| Leaf Shape: | Ovate | *Phytophthora* Gene | Rps1c |
| Seed Coat Color: | Yellow | Hypocotyl Length | Long |
| Hypocotyl Color: | Green with Bronze band | Soybean Cyst Nematode | R 3, 14 |
| Maturity Group | 4 | Frogeye Leaf Spot | Susc. |
| Relative Maturity | 4-3 | | |

The present invention provides methods and composition relating to plants, seeds and derivatives of the soybean cultivar S07-02JR409106. Soybean cultivar S07-02JR409106 has superior characteristics. The S07-02JR409106 line has been selfed sufficient number of generations to provide a stable and uniform plant variety.

Cultivar S07-02JR409106 shows no variants other than expected due to environment or that normally would occur for almost any characteristic during the course of repeated sexual reproduction. Some of the criteria used to select in various generations may include: seed yield, emergence, appearance, disease tolerance, maturity, plant height, and shattering data.

The inventor believes that S07-02JR409106 is similar in relative maturity to the comparison varieties. However, as shown in the tables, S07-02JR409106 differs from these cultivars.

Direct comparisons were made between S07-02JR409106 and the listed commercial varieties. Traits measured may include yield, maturity, lodging, plant height, branching, field emergence, and shatter. The results of the comparison are presented in the table below. The number of tests in which the varieties were compared is shown with the environments, mean and standard deviation for some traits.

The present invention S07-02JR409106 can carry genetic engineered recombinant genetic material to give improved traits or qualities to the soybean. For example, but not limited to, the present invention can carry the glyphosate resistance gene for herbicide resistance as taught in the Monsanto patents (WO92/00377, WO92/04449, U.S. Pat. No. 5,188,642 and U.S. Pat. No. 5,312,910) or STS mutation for herbicide with two replications in about 20-25 locations. The data shown in FIG. 1 is only charted if there are at least 3 or more locations.

The present invention (also known as 02JR409106) differs from the mean of the comparison commercial and experimental soybean lines in that the present soybean cultivar is across numerous locations, exceeding the mean yield of the group of soybeans (GRP_MN) that were tested and displayed in this geographic segment chart (GSEGC). As shown in FIG. 1 S07-02JR409106 has shown superior yield across the Central and the Midsouth regions. In the Central, it averaged 105% of Group Mean, while in the Midsouth it averaged 106% of Group Mean.

Figure 2:
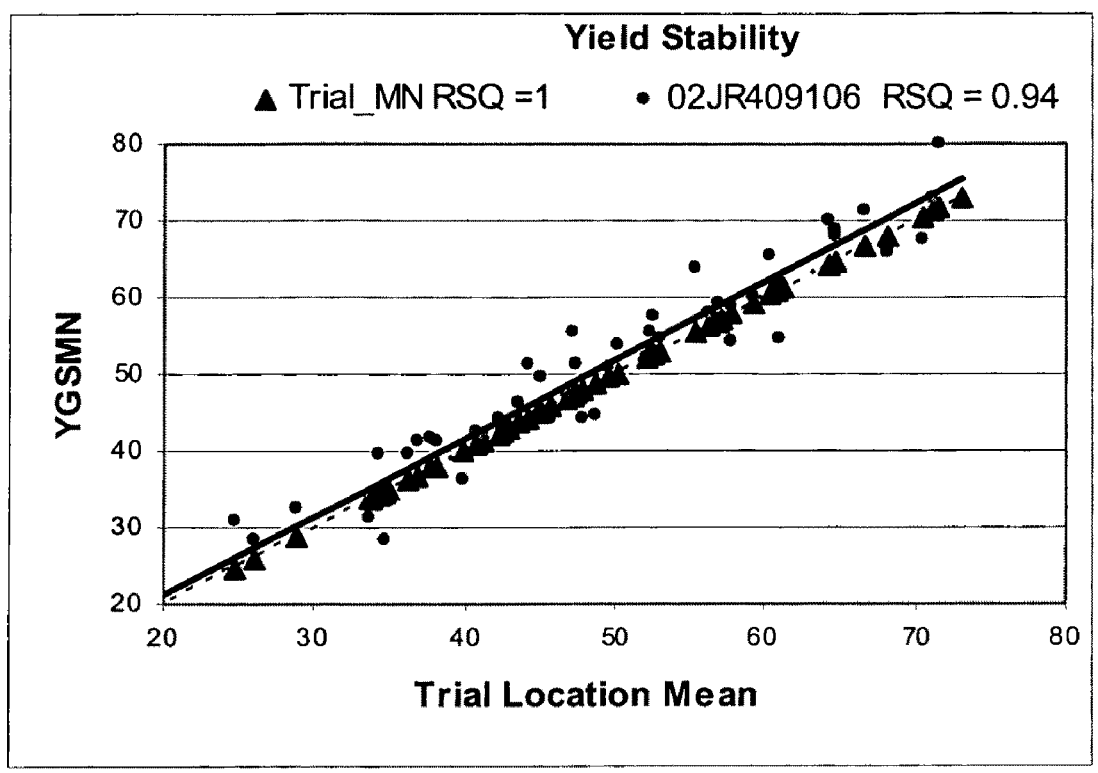
FIG. 2 shows the Group Mean chart (GRP_MN=Group Mean) of Grain Yield at standard moisture for S07-02JR409106. This chart shows Yield Stability–Win>5% of trial mean, Tie+ or –5% of trial mean, Losses <5% of trial mean. The chart's vertical axis=yield of target variety, its horizontal axis=location average yield. When the target variety line is above the location average line this is desirable. The RSQ of the target variety shows a number. This number when it is closest to 1=yield stability.

The present invention S07-02JR409106 is employed in a trial with a number of environments. The results of the grain yield at standard moisture (YGSMN) are shown in FIG. 2. The present invention is also superior to the Group Mean across most environmental conditions, with only a few outliers below the Group mean scattered evenly among all yield levels, most of the data points are at or above the Group mean. These tests allow the usefulness of the invention to be shown in light of the environmental genetic interactions.

TABLE 1

Research Data Yield Performance Chart

| VHNO | YGSMN | MRTYN | HLDGR | PLHTN | GLDGR | PLCNR | PRR_R | IC_R | SDS_R | FELSR | GS_R | EMRGR | TESTP |
|---|---|---|---|---|---|---|---|---|---|---|---|---|---|
| 94M50 | 50.6 | 139.5 | 3.0 | 85.8 | 2.1 | 7.4 | 3.5 | 7.7 | 3.0 | 2.0 | 5.5 | 2.9 | 106.2 |
| S07-02JR409106 | 50.2 | 138.4 | 3.6 | 84.5 | 3.5 | 6.5 | 3.3 | 7.6 | 3.9 | 5.0 | 5.0 | 2.8 | 104.1 |
| 4212RR/STS/N | 49.7 | 138.3 | 2.7 | 80.3 | 1.7 | 7.0 | 3.0 | 4.4 | 3.1 | 1.8 | 4.3 | 2.5 | 102.2 |
| 4422-4 | 49.4 | 139.7 | 2.7 | 80.5 | 2.1 | 7.4 | 3.6 | 5.2 | 3.2 | 2.0 | 4.2 | 2.8 | 102.4 |
| 4512RR/N | 49.2 | 140.0 | 3.2 | 92.7 | 3.5 | 8.1 | 3.8 | 7.9 | 3.2 | 5.0 | 4.1 | 3.2 | 100.9 |
| AG3905 | 48.8 | 136.3 | 3.2 | 87.5 | 3.8 | 7.4 | 3.9 | 6.6 | 3.6 | 4.8 | 3.2 | 3.0 | 101.5 |
| S41-M5 | 48.6 | 135.3 | 4.1 | 90.7 | 4.6 | 6.2 | 4.0 | 4.7 | 4.1 | 1.3 | 3.0 | 3.1 | 99.2 |
| S43-B1 | 47.5 | 137.8 | 3.9 | 87.5 | 3.6 | 7.0 | 3.1 | 5.6 | 3.0 | 4.5 | 4.4 | 2.6 | 97.1 |
| 94B13 | 47.4 | 134.0 | 3.6 | 87.4 | 4.2 | 7.2 | 3.6 | 6.0 | 4.2 | 2.8 | 2.5 | 2.6 | 97.4 |
| S44-J5 | 46.6 | 139.5 | 3.4 | 91.6 | 4.7 | 6.9 | 3.9 | 6.6 | 2.4 | 2.0 | 4.1 | 3.3 | 94.9 |
| Environments | 58.0 | 17.0 | 24.0 | 28.0 | 5.0 | 2.0 | 2.0 | 2.0 | 7.0 | 2.0 | 4.0 | 20.0 | 58.0 |
| Grand Mean | 49.2 | 138.7 | 3.2 | 87.7 | 3.1 | 7.1 | 3.4 | 6.4 | 3.6 | 3.1 | 4.4 | 2.9 | 101.8 |
| Check Mean | 48.6 | 137.8 | 3.3 | 87.1 | 3.4 | 7.2 | 3.6 | 6.1 | 3.3 | 2.9 | 3.9 | 2.9 | 100.2 |
| LSD (0.05) | 1.8 | 1.4 | 0.3 | 2.4 | 1.1 | 1.1 | 0.0 | 1.7 | 0.9 | 1.9 | 1.6 | 0.3 | 0.0 | resistance. Additional traits carried in transgenes or mutation can be transferred into the present invention. Some of these genes include genes that give disease resistance to *sclerotinia* such as the oxalate oxidase (Ox Ox) gene as taught in PCT/FR92/00195 Rhone Polunc and/or an oxalate decarboxylase gene for disease resistance or genes designed to alter the soybean oil within the seed such as desaturase, thioesterase genes (shown in EP0472722, U.S. Pat. No. 5,344,771) or genes designed to alter the soybean's amino acid characteristics. This line can be crossed with another soybean line which carries a gene that acts to provide herbicide resistance or alter the saturated and/or unsaturated fatty acid content of the oil within the seed, or the amino acid profile of the seed.

The present invention S07-02JR409106 is employed in a number of plot repetitions to establish trait characteristics.

Geographic Summary

The target variety yield is given as a percent of the trial average at all locations shown in FIG. 1 and each geographic segment West to East or Central (Cntrl) to South East where there are three or more locations. The plots for these trials are two row 13 to 17.5 foot plots planted in 30-inch row spacing. The plants in the plots are a combination of experimental material and commercial material. There are usually 36 varieties and there are approximately 250 plants of each variety As the previous chart indicates S07-02JR409106 is most similar to Garst Brand 4512RR/N but can be differentiated on the basis of flower color and *Phytophthora* Root Rot Resistance gene. S07-02JR409106 has white flowers and has the major *Phytophthora* gene Rps1c while Garst Brand 4512RR/N has purple flowers and the Rps1a gene. S07-02JR409106 is also similar to Syngenta Seeds Inc. S07-02JR409114 but can be differentiated based on maturity, S07-02JR409114 is significantly later (LSD.05)=1 than S07-02JR409106. S07-02JR409106 can be differentiated from 03JR103829 on the basis of hilum color, this line has black hilum while 03JR103829 has brown hilum. The yield and other data is a snapshot of each of these lines' results in the specific environment and will differ when other environmental interactions are measured.

This invention also is directed to methods for producing a new soybean plant by crossing a first parent plant with a second parent plant wherein the first or second parent plant is the present invention. Additionally, the present invention may be used in the variety development process to derive progeny in a breeding population or crossing. Further, both first and second parent plants can be or be derived from the soybean line S07-02JR409106. A variety of breeding methods can be selected depending on the mode of reproduction, the trait, the condition of the germplasm. Thus, any such methods using the S07-02JR409106 are part of this invention: selfing, backcrosses, recurrent selection, mass selection and the like.

The scope of the present invention includes use of marker methods. In addition to phenotypic observations, the genotype of a plant can also be examined. There are many techniques or methods known which are available for the analysis, comparison and characterization of plant's genotype and for understanding the pedigree of the present invention and identifying plants that have the present invention as an ancestor; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites.

A backcross conversion, transgene, or genetic sterility factor, may be in an embodiment of the present invention. Markers can be useful in their development, such that the present invention comprising backcross conversion(s), transgene(s), or genetic sterility factor(s), and are identified by having a molecular marker profile with a high percent identity such as 95%, 96%, 97%, 98%, 99%, 99.5% or 99.9% identical to the present invention.

These embodiments may be detected using measurements by either percent identity or percent similarity to the deposited material. These markers may detect progeny plants identifiable by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from an embodiment of the present soybean variety. Such progeny may be further characterized as being within a pedigree distance of 1, 2, 3, 4 or 5 or more cross-pollinations to a soybean plant other than the present invention or a plant that has the present invention as a progenitor. Molecular profiles may be identified with SNP, Single Nucleotide Polymorphism, or other tools also.

Traits are average values for all trial locations, across all years in which the data was taken. In addition to the visual traits that are taking the genetic characteristic of the plant can also be characterised by its genetic marker profile. The profile can interpret or predict the pedigree of the line, the relation to another variety, determine the accuracy of a listed breeding strategy, or invalidate a suggested pedigree. Soybean linkage maps were known by 1999 as evidenced in Cregan et. al, "An Integrated Genetic Linkage Map of the Soybean Genome" Crop Science 39:1464 1490 (1999); and using markers to determine pedigree claims was discussed by Berry et al., in "Assessing Probability of Ancestry Using Simple Sequence Repeat Profiles: Applications to Maize Inbred Lines and Soybean Varieties" Genetics 165:331 342 (2003), each of which are incorporated by reference herein in their entirety. Markers include but are not limited to Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). There are known sets of public markers that are being examined by ASTA and other industry groups for their applicability in standardizing determinations of what constitutes an essentially derived variety under the US Plant Variety Protection Act. However, these standard markers do not limit the type of marker and marker profile which can be employed in breeding or developing backcross conversions, or in distinguishing varieties or plant parts or plant cells, or verify a progeny pedigree. Primers and PCR protocols for assaying these and other markers are disclosed in the Soybase (sponsored by the USDA Agricultural Research Service and Iowa State University) located at the world wide web at 129.186.26.94/SSR.html.

Additionally, these markers such as SSRs, RFLP's, SNPs, Ests, AFLPs, gene primers, and the like can be developed and employed to identify genetic alleles which have an association with a desired trait. The allele can be used in a marker assisted breeding program to move traits (native, normative (from a different species, or transgenes)) into the present invention. The value of markers includes allowing the introgression of the allele(s)/trait(s) into the desired germplasm with little to no superfluous germplasm being dragged from the allele/trait donor plant into the present invention. This results in formation of the present invention for example, cyst nematode resistance, brown stem rot resistance, aphid resistance, *Phytophthora* resistance, IDC resistance, BT genes, male sterility genes, glyphosate tolerance genes or drought tolerance genes. Additionally, the invention through transgenes, or if a native trait through markers or backcross breeding, can include a polynucleotide encoding phytase, FAD-2, FAD-3, galactinol synthase or a raffinose synthetic enzyme; or a polynucleotide conferring resistance to soybean cyst nematode, brown stem rot, *phytophthora* root rot, or sudden death syndrome or resistance or tolerance to FUNGAL DISEASES such as: *Alternaria* spp., *Agrobacterium rhizogenes, Calonectria crotalariae, Cercospora kikuchii, Cercospora sojina, Choanephora infundibulifera, Colletotrichum* spp., *Corynespora cassiicola, Curtobacterium flaccumfaciens, Dactuliochaeta glycines, Diaporthe phaseolorum, Fusarium oxysporum, Macrophomina phaseolina, Microsphaera difusa, Peronospora manshurica, Phakopsora pachyrhizi, Phialophora gregata, Phomopsis phaseolorum, Phyllosticta sojicola, Phytophthora megasperma, Pseudomonas syringae, Pythium* spp., *Rhizoctonia solana, Sclerotinia sclerotiorum, Sclerotium rolfsii, Septoria glycines, Sphaceloma glycines, Thielaviopsis basicota*.; BACTERIAL and VIRAL DISEASES such as: *Xanthomonas campestres*, Cowpea Chlorotic Mottle Virus (CCMV), Peanut Mottle Virus (PMV), Tobacco Streak Virus (TSV), Bean Yellow Mosaic Virus (BYMV), Black Gram Mottle Virus (BGMV), Cowpea Mild Mottle Virus (CMMV), Cowpea Severe Mosaic Virus (CSMV), Indonesian Soybean Dwarf Virus (ISDV), Mung Bean Yellow Mosaic Virus (MYMV), Peanut Stripe Virus (VPMM), Soybean Chlorotic Mottle Virus, Soybean Crinkle Leaf Virus, Soybean Yellow Vein Virus (SYVV), Tobacco Mosaic Virus (TMV); NEMATODES such as: *Belonolaimus gracilis, Meloidogyne* spp, *Rotylenchulus reniformis, Pratylenchus* spp., *Hoplolaimus sulumbus, Heterodera schachtii.*

Many traits have been identified that are not regularly selected for in the development of a new cultivar. Using materials and methods well known to those persons skilled in the art, traits that are capable of being transferred, to cultivar of the present invention include, but are not limited to, herbicide tolerance, resistance for bacterial, fungal, or viral disease, nematode resistance, insect resistance, enhanced nutritional quality, such as oil, starch and protein content or quality, improved performance in an industrial process, altered reproductive capability, such as male sterility or male/female fertility, yield stability and yield enhancement. Other traits include the production of commercially valuable enzymes or metabolites within the present invention.

A transgene typically comprises a nucleotide sequence whose expression is responsible or contributes to the trait, under the control of a promoter capable of directing the expression of the nucleotide sequence at the desired time in the desired tissue or part of the plant. Constitutive, tissue-specific or inducible promoters are well known in the art and have different purposes and each could be employed. The transgene(s) may also comprise other regulatory elements such as for example translation enhancers or termination signals. The transgene may be adapted to be transcribed and translated into a protein, or to encode RNA in a sense or antisense orientation such that it is not translated or only partially translated.

Transgenes may be directly introduced into the cultivar using genetic engineering and transformation techniques well known in the art or introduced into the cultivar through a process which uses a donor parent which has the transgene(s) already introgressed. This process of introduction of a transgene(s) or native/non-native traits into the cultivar may use the donor parent in a marker assisted trait conversion process, where the trait may be moved for example by backcrossing using the markers for selection of subsequent generations.

The laboratory-based techniques described above, in particular RFLP and SSR, can be used in such backcrosses to identify the progenies having the highest degree of genetic identity with the recurrent parent. This permits one to accelerate the production of soybean cultivars having at least 90%, 95%, 99% genetic, or genetically identical to the recurrent parent, and further comprising the trait(s) introgressed from the donor parent. Such determination of genetic identity can be based on markers used in the laboratory-based techniques described above.

The last backcross generation is then selfed to give pure breeding progeny for the gene(s) being transferred. The resulting plants have essentially all of the morphological and physiological characteristics of cultivar of the present invention, in addition to the gene trait(s) transferred to the inbred. The exact backcrossing protocol will depend on the trait being altered to determine an appropriate testing protocol.

Although backcrossing methods are simplified when the trait being transferred is a dominant allele, a recessive allele may also be transferred. In this instance it may be necessary to introduce a test of the progeny to determine if the desired trait has been successfully transferred.

The cultivar of the invention can also be used for transformation where exogenous genes are introduced and expressed by the cultivar of the invention. Genetic variants created either through traditional breeding methods using cultivar of the present invention or through transformation of such cultivar by any of a number of protocols known to those of skill in the art are intended to be within the scope of this invention (see e.g. Trick et al. (1997) Recent Advances in Soybean Transformation, Plant Tissue Culture and Biotechnology, 3:9-26).

Transformation methods are means for integrating new genetic coding sequences (transgenes) into the plant's genome by the incorporation of these sequences into a plant through man's assistance. Many dicots including soybeans can easily be transformed with *Agrobacterium*. Methods of introducing desired recombinant DNA molecule into plant tissue include the direct infection or co-cultivation of plant cells with *Agrobacterium tumefaciens*, Horsch et al., Science, 227:1229 (1985). Descriptions of *Agrobacterium* vector systems and methods are shown in Gruber, et al., "Vectors for Plant Transformation, in Methods in Plant Molecular Biology & Biotechnology" in Glich et al., (Eds. pp. 89-119, CRC Press, 1993). Transformed plants obtained via protoplast transformation are also intended to be within the scope of this invention. The most common method of transformation after the use of *agrobacterium* is referred to as gunning or microprojectile bombardment. This process has small gold-coated particles coated with DNA (including the transgene) shot into the transformable material. Techniques for gunning DNA into cells, tissue, explants, meristems, callus, embryos, and the like are well known in the prior art.

The DNA used for transformation of these plants clearly may be circular, linear, and double or single stranded.

Some of the time the DNA is in the form of a plasmid. The plasmid may contain additional regulatory and/or targeting sequences which assist the expression or targeting of the gene in the plant. The methods of forming plasmids for transformation are known in the art. Plasmid components can include such items as: leader sequences, transit polypeptides, promoters, terminators, genes, introns, marker genes, etc. The structures of the gene orientations can be sense, antisense, partial antisense or partial sense: multiple gene copies can be used.

After the transformation of the plant material is complete, the next step is identifying the cells or material, which has been transformed. In some cases, a screenable marker is employed such as the beta-glucuronidase gene of the uidA locus of *E. coli*. Then, the transformed cells expressing the colored protein are selected for either regeneration or further use. In many cases, a selectable marker identifies the transformed material. The putatively transformed material is exposed to a toxic agent at varying concentrations. The cells not transformed with the selectable marker, which provides resistance to this toxic agent, die. Cells or tissues containing the resistant selectable marker generally proliferate. It has been noted that although selectable markers protect the cells from some of the toxic affects of the herbicide or antibiotic, the cells may still be slightly affected by the toxic agent by having slower growth rates. If the transformed materials are cell lines then these lines are used to regenerate plants. The cells' lines are treated to induce tissue differentiation. Methods of regeneration of plants are well known in the art. General methods of culturing plant tissues are provided for example by Maki et al. "Procedures for Introducing Foreign DNA into Plants" in Methods in Plant Molecular Biology & Biotechnology, Glich et al. (Eds. pp. 67-88 CRC Press, 1993); and by Phillips et al. "Cell-Tissue Culture and In-Vitro Manipulation" in Soybean & Soybean Improvement, 3rd Edition Sprague et al. (Eds. pp. 345-387) American Society of Agronomy Inc. et al. 1988.

The plants from the transformation process or the plants resulting from a cross using a transformed line or the progeny of such plants which carry the transgene are transgenic plants.

The genes responsible for a specific gene trait are generally inherited through the nucleus. Known exceptions are, e.g. the genes for male sterility, some of which are inherited cytoplasmically, but still act as single gene traits. The following U.S. patents list alleles or transgenes that produce the trait of mail sterility in soybeans; 4,763,441; 4,648,204; 4,545,146; 6,046,385. The male sterility trait allows for hybrid soybean production and breeding. In a preferred embodiment, a transgene to be introgressed into the cultivar S07-02JR409106 is integrated into the nuclear genome of the donor, non-recurrent parent or the transgene is directly transformed into the nuclear genome of cultivar S07-02JR409106. In another embodiment of the invention, a transgene to be introgressed into cultivar S07-02JR409106 is integrated into the plastid genome of the donor, non-recurrent parent or the transgene is directly transformed into the plastid genome of cultivar S07-02JR409106. In a further embodiment of the invention, a plastid transgene comprises a gene that has transcribed from a single promoter, or two or more genes transcribed from a single promoter.

A non-exclusive list of traits or nucleotide sequences capable of being transferred into cultivar S07-02JR409106, using material and methods well known to those persons skilled in the art are as follows: genetic factor(s) responsible for resistance to brown stem rot (U.S. Pat. No. 5,689,035) or resistance to cyst nematodes (U.S. Pat. No. 5,491,081); a transgene encoding an insecticidal protein, such as, for example, a crystal protein of *Bacillus thuringiensis* or a vegetative insecticidal protein from *Bacillus cereus*, such as VIP3 (see, for example, Estruch et al. Nat Biotechnol (1997) 15:137-41; a herbicide tolerance transgene whose expression renders plants tolerant to the herbicide, for example, expression of an altered acetohydroxyacid synthase (AHAS) enzyme confers upon plants tolerance to various imidazolinone or sulfonamide herbicides (U.S. Pat. No. 4,761,373.) Other traits capable of being transformed into cultivar S07-02JR409106 include, for example, a non-transgenic trait conferring to cultivar S07-02JR409106 tolerance to imidazolinones or sulfonylurea herbicides; a transgene encoding a mutant acetolactate synthase (ALS) that renders plants resistant to inhibition by sulfonylurea herbicides (U.S. Pat. No. 5,013,659); a gene encoding a mutant glutamine synthetase (GS) resistant to inhibition by herbicides that are known to inhibit GS, e.g. phosphinothricin and methionine sulfoximine (U.S. Pat. No. 4,975,374); and a *Streptomyces* bar gene encoding a phosphinothricin acetyl transferase resulting in tolerance to the herbicide phosphinothricin or glufosinate (U.S. Pat. No. 5,489,520.)

Other genes capable of being transferred into the cultivar S07-02JR409106 of the invention include toleration to inhibition by cyclohexanedione and aryloxyphenoxypropanoic acid herbicides (U.S. Pat. No. 5,162,602), which is conferred by an altered acetyl coenzyme A carboxylase (ACCase); transgenic glyphosate tolerant plants, which tolerance is conferred by an altered 5-enolpyruvyl-3-phosphoshikimate (EPSP) synthase gene; tolerance to a protoporphyrinogen oxidase inhibitor, which is achieved by expression of a tolerant protoporphyrinogen oxidase enzyme in plants (U.S. Pat. No. 5,767,373.) Genes encoding altered protox resistant to a protox inhibitor can also be used in plant cell transformation methods. For example, plants, plant tissue or plant cells transformed with a transgene can also be transformed with a gene encoding an altered protox (See U.S. Pat. No. 6,808,904 incorporated by reference) capable of being expressed by the plant. The thus-transformed cells are transferred to medium containing the protox inhibitor wherein only the transformed cells will survive. Protox inhibitors contemplated to be particularly useful as selective agents are the diphenylethers (e.g. acifluorfen, 5-[2-chloro-4-(trifluoromethyl)phenoxy]-2-nitrobezoic acid; its methyl ester, or oxyfluorfen, 2-chloro-1-(3-ethoxy-4-nitrophenoxy)-4-(trifluorobenzene)), oxidiazoles, (e.g. oxidiazon, 3-[2,4-dichloro-5-(1-methylethoxy)phenyl]-5-(1,1-dimethylethyl)-1,3,4-oxadiazol-2-(3H)-one), cyclic imides (e.g. S-23142, N-(4-chloro-2-fluoro-5-propargyloxyphenyl)-3,4,5,6-tetrahydrophthalimide; chlorophthalim, N-(4-chlorophenyl)-3,4,5,6-tetrahydrophthalimide), phenyl pyrazoles (e.g. TNPP-ethyl, ethyl 2-[1-(2,3,4-trichlorophenyl)-4-nitropyrazolyl-5-oxy]propionate; M&B 39279), pyridine derivatives (e.g. LS 82-556), and phenopylate and its O-phenylpyrrolidino- and piperidinocarbamate analogs and bicyclic triazolones as disclosed in the International patent application WO 92/04827; EP 532146).

The method is applicable to any plant cell capable of being transformed with an altered protox-encoding gene, and can be used with any transgene of interest. Expression of the transgene and the protox gene can be driven by the same promoter functional on plant cells, or by separate promoters.

Modified inhibitor-resistant protox enzymes of the present invention are resistant to herbicides that inhibit the naturally occurring protox activity. The herbicides that inhibit protox include many different structural classes of molecules (Duke et al., Weed Sci. 39: 465 (1991); Nandihalli et al., Pesticide Biochem. Physiol. 43: 193 (1992); Matringe et al., FEBS Lett. 245: 35 (1989); Yanase and Andoh, Pesticide Biochem. Physiol. 35: 70 (1989)), including the diphenylethers {e.g. acifluorifen, 5-[2-chloro-4-(trifluoromethyl)phenoxy]-2-nitrobezoic acid; its methyl ester; or oxyfluorfen, 2-chloro-1-(3-ethoxy-4-nitrophenoxy)-4-(trifluorobenzene)}, oxidiazoles (e.g. oxidiazon, 3-[2,4-dichloro-5-(1-methylethoxy)phenyl]-5-(1,1-dimethylethyl)-1,3,4-oxad iazol-2-(3H)-one), cyclic imides (e.g. S-23142, N-(4-chloro-2-fluoro-5-propargyloxyphenyl)-3,4,5,6-tetrahydrophthalimide; chlorophthalim, N-(4-chlorophenyl)-3,4,5,6-tetrahydrophthalimide), phenyl pyrazoles (e.g. TNPP-ethyl, ethyl 2-[1-(2,3,4-trichlorophenyl)-4-nitropyrazolyl-5-oxy]propionate; M&B 39279), pyridine derivatives (e.g. LS 82-556), and phenopylate and its O-phenylpyrrolidino- and piperidinocarbamate analogs.

Direct selection may be applied where the trait acts as a dominant trait. An example of a dominant trait is herbicide tolerance. For this selection process, the progeny of the initial cross are sprayed with the herbicide prior to the backcrossing. The spraying eliminates any plant that does not have the desired herbicide tolerance characteristic, and only those plants that have the herbicide tolerance gene are used in the subsequent backcross. This process is then repeated for the additional backcross generations.

In yet another embodiment of the present invention, a transgene transformed or introgressed into cultivar S07-02JR409106 comprises a gene conferring tolerance to a herbicide and at least another nucleotide sequence for another trait, such as for example, insect resistance or tolerance to another herbicide. Another gene capable of being transferred into the cultivar S07-02JR409106 of the invention expresses thioredoxin and thioredoxin reductase enzymes for modifying grain digestibility and nutrient availability (U.S. Pat. Appl. No. 20030145347.)

Further reproduction of the cultivar can occur by tissue culture and regeneration. Tissue culture of various tissues of soybeans and regeneration of plants therefrom is well known and widely published. For example, reference may be had to Komatsuda, T. et al., "Genotype X Sucrose Interactions for Somatic Embryogenesis in Soybean," Crop Sci. 31:333-337 (1991); Stephens, P. A. et al., "Agronomic Evaluation of Tissue-Culture-Derived Soybean Plants," Theor. Appl. Genet. (1991) 82:633-635; Komatsuda, T. et al., "Maturation and Germination of Somatic Embryos as Affected by Sucrose and Plant Growth Regulators in Soybeans *Glycine gracilis* Skvortz and *Glycine max* (L.) Merr.," Plant Cell, Tissue and Organ Culture, 28:103-113 (1992); Dhir, S. et al., "Regeneration of Fertile Plants from Protoplasts of Soybean (*Glycine max* L. Merr.): Genotypic Differences in Culture Response," Plant Cell Reports (1992) 11:285-289; Pandey, P. et al., "Plant Regeneration from Leaf and Hypocotyl Explants of *Glycine wightii* (W. and A.) VERDC. var *longicauda*," Japan J. Breed. 42:1-5 (1992); and Shetty, K., et al., "Stimulation of In Vitro Shoot Organogenesis in *Glycine max* (Merrill.) by Allantoin and Amides," Plant Science 81:(1992) 245-251; as well as U.S. Pat. No. 5,024,944, issued Jun. 18, 1991 to Collins et al. and U.S. Pat. No. 5,008,200, issued Apr. 16, 1991 to Ranch et al. Thus, another aspect of this invention is to provide cells that upon growth and differentiation produce soybean plants having all or essentially all the physiological and morphological characteristics of cultivar S07-02JR409106. The disclosures, publications, and patents that are disclosed herein are all hereby incorporated herein in their entirety by reference.

The seed of soybean cultivar S07-02JR409106 further comprising one or more specific, single gene traits, the plant produced from the seed, the hybrid soybean plant produced from the crossing of the cultivar with any other soybean plant, hybrid seed, and various parts of the hybrid soybean plant can be utilized for human food, livestock feed, and as a raw material in industry.

Soybean is the world's leading source of vegetable oil and protein meal. The oil extracted from soybeans is used for cooking oil, margarine, and salad dressings. Soybean oil is composed of saturated, monounsaturated and polyunsaturated fatty acids. It has a typical composition of 11% palmitic, 4% stearic, 25% oleic, 50% linoleic and 9% linolenic fatty acid content ("Economic Implications of Modified Soybean Traits Summary Report", Iowa Soybean Promotion Board & American Soybean Association Special Report 92S, May 1990.) Changes in fatty acid composition for improved oxidative stability and nutrition are constantly sought after. (U.S. Pat. No. 5,714,670 Soybeans Having Low Linolenic Acid and Low Palmitic Acid Contents; U.S. Pat. No. 5,763,745 Soybeans Having Low Linolenic Acid Content and Palmitic Acid Content of at Least Eleven Percent; U.S. Pat. No. 5,714,668 Soybeans Having Low Linolenic Acid And Elevated Stearic Acid Content; U.S. Pat. No. 5,714,669 A17 Soybeans Having Low Linolenic Acid Content and Descendents; U.S. Pat. No. 5,710,369 A16 Soybeans Having Low Linolenic Acid Content and Descendents; U.S. Pat. No. 5,534,425 Soybeans Having Low Linolenic Acid Content and Method of Production; U.S. Pat. No. 5,750,844 Soybeans Capable of Forming a Vegetable Oil Having Specified Concentrations of Palmitic and Stearic Acids; U.S. Pat. No. 5,750,845 Soybeans Capable of Forming a Vegetable Oil Having a Low Saturated Fatty Acid Content; U.S. Pat. No. 5,585,535 Soybeans and Soybean Products Having Low Palmitic Acid Content; U.S. Pat. No. 5,850,029 Soybean Designated AX7017-1-3; U.S. Pat. No. 5,663,485 Soybean Designated A89-259098; U.S. Pat. No. 5,684,230 Soybean Designated AX 4663-5-4-5; U.S. Pat. No. 5,684,231 Soybean Designated A1937 NMU-85; U.S. Pat. No. 5,714,672 Soybean Designated ElginEMS-421; U.S. Pat. No. 5,602,311 Soybeans and Soybean Products Having High Palmitic Acid Content; U.S. Pat. No. 5,795,969 Soybean Vegetable Oil Having Elevated Concentrations of Both Palmitic and Stearic Acid; U.S. Pat. No. 5,557,037 Soybeans Having Elevated Contents of Saturated Fatty Acids; U.S. Pat. No. 5,516,980 Soybean Variety XB37ZA; U.S. Pat. No. 5,530,183 Soybean Variety 9253; U.S. Pat. No. 5,750,846 Elevated Palmitic Acid Production in Soybeans; U.S. Pat. No. 6,060,647 Elevated Palmitic Acid Production in Soybeans; U.S. Pat. No. 6,025,509 Elevated Palmitic Acid Production in Soybeans; U.S. Pat. No. 6,133,509 Reduced Linolenic Acid Production in Soybeans; U.S. Pat. No. 5,986,118 Soybean Vegetable Oil Possessing a Reduced Linolenic Acid Content; U.S. Pat. No. 5,850,030 Reduced Linolenic Acid Production in Soybeans). Industrial uses of soybean oil that is subjected to further processing include ingredients for paints, plastics, fibers, detergents, cosmetics, and lubricants. Soybean oil may be split, inter-esterified, sulfurized, epoxidized, polymerized, ethoxylated, or cleaved. Designing and producing soybean oil derivatives with improved functionality, oliochemistry is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils.

The techniques of seed treatment application are well known to those skilled in the art, and they may be used readily in the context of the present invention. The seed treating compositions can be applied to the seed as slurry, mist or a soak or other means know to those skilled in the art of seed treatment. There also may be mentioned, e.g., film coating or encapsulation. The coating processes are well known in the art, and employ, for seeds, the techniques of film coating or encapsulation, or for the other multiplication products, the techniques of immersion. Needless to say, the method of application of the compositions to the seed may be varied and is intended to include any technique that is to be used.

The term "fungicide" as utilized herein is intended to cover compounds active against phytopathogenic fungi that may belong to a very wide range of compound classes. Examples of compound classes to which the suitable fungicidally active compound may belong include both room temperature (25.degree. C.) solid and room temperature liquid fungicides such as: triazole derivatives, strobilurins, carbamates (including thio- and dithiocarbamates), benzimidazoles (thiabendazole), N-trihalomethylthio compounds (captan), substituted benzenes, carboxamides, phenylamides and phenylpyrroles, and mixtures thereof.

The present invention includes a method for preventing damage by a pest to a seed of the present invention and/or shoots and foliage of a plant grown from the seed of the present invention. Broadly the method includes treating the seed of the present invention with a pesticide. The pesticide is a composition that stops pests including insects, diseases, and the like. Broadly compositions for seed treatment can include but is not limited to any of one of the following: an insecticide, or a fungicide.

The method comprising treating an unsown seed of the present invention with neonicotinoid composition. One of these compositions is thiamethoxam. Additionally, the neonicotinoid composition can include at least one pyrethrin or synthetic pyrethroid, to reduce pest damage. More specifically there is a method of seed treatment which employs thiamethoxam and at least one pyrethrin or pyrethroid are comprised within a seed coating treated on the seed of the present invention. The combination, if thiamethoxam is employed, can be coated at a rate which is greater than 200 gm/100 kg of seed. The method includes having at least one of the pyrethroids being a systemic insecticide.

The pyrethrin or synthetic pyrethroid, if employed can be selected from the group consisting of taufluvalinate, flumethrin, trans-cyfluthrin, kadethrin, bioresmethrin, tetramethrin, phenothrin, empenthrin, cyphenothrin, prallethrin, imiprothrin, allethrin and bioallethrin.

The fungicidally active compounds and/or the insecticidal active compounds are employed in a fungicidally and/or insecticidally effective amount in the composition. Mixtures of one or more of the following active compounds are usable as an active component treatment of the seed of the present invention. Examples of suitable individual compounds for use in seed treatments are listed below. Where known, the common name is used to designate the individual compounds (q.v. the Pesticide Manual, 12th edition, 2001, British Crop Protection Council).

Suitable triazole derivatives include propiconazole, difenconazole, tebuconazole, tetraconazole and triticonazole. Suitable strobilurins include trifloxystrobin, azoxystrobin, kresoxim-methyl and picoxystrobin. Suitable carbamates include thiram. Suitable substituted benzenes include PCNB and chlorothalonil. Suitable carboxamides include carboxin.

Specific phenylamides usable in the compositions and methods include metalaxyl. A specific phenylpyrrole usable in the composition is fludioxonil.

Other suitable fungicidal compounds that maybe mentioned are Benomyl (also known as Benlate), Bitertanol, Carbendazim, Capropamid, Cymoxanil, Cyprodinil, Ethirimol, Fenpiclonil, Fenpropimorph, Fluquinconazole, Flutolanil, Flutriafol, Fosetyl-aluminum, Fuberidazole, Guazatine, Hymexanol, Kasugamycin, Imazalil, Imibenconazole, Iminoctadine-triacetate, Ipconazole, Iprodione, Mancozeb, Maneb, Mepronil, Metalaxyl, Metalaxyl-M (Mefenoxam), Metconazole, Metiram, MON 65500 (Silthiopham-ISO proposed), Myclobutanil, Nuarimol, Oxadixyl, Oxine-copper, Oxolinic acid, Pefurazoate, Pencycuron, Prochloraz, Propamocarb hydrochloride, Pyroquilon, Silthiopham—see MON 65500, Tecnazene, Thifluzamide, Thiophenate-methyl, Tolclofos-methyl, Triadimenol, Triazoxide and Triflumizole.

The fungicidally active compounds and/or the insecticidal active compounds are employed in a fungicidally and/or insecticidally effective amount in the composition. Mixtures of one or more of the following active compounds also are usable as an active component treatment of the seed of the present invention.

In one seed treatment, mixtures of at least one ambient liquid fungicide (for example, a phenylamide such as R-metalaxyl) and at least one ambient solid fungicide (for example, a phenylpyrrole such as fludioxonil) could be employed. The apparatus for providing the appropriate amount of seed treatment of a specific chemical composition for a seed are well known in the seed coating industry (See, for example, U.S. Pat. Nos. 5,632,819 and 5,891,246).

Soybean is not just a seed it is also used as a grain. The grain is used as a food source for both animals and humans. Soybean is widely used as a source of protein for animal feeds for poultry, swine and cattle. The soybean grain is a commodity. The soybean commodity plant products include but are not limited to protein concentrate, protein isolate, soybean hulls, meal, flower, oil and the whole soybean itself. During processing of whole soybeans, the fibrous hull is removed and the oil is extracted. The remaining soybean meal is a combination of carbohydrates and approximately 50% protein. For human consumption soybean meal is made into soybean flour that is processed to protein concentrates used for meat extenders or specialty pet foods. Production of edible protein ingredients from soybean offers a healthy less expensive replacement for animal protein in meats as well as dairy-type products.

Deposit Information

Applicants have made a deposit of at least 2500 seeds of soybean cultivar S07-02JR409106 with the American Type Culture Collection (ATCC), Manassas, Va. 20110 on Feb. 28, 2011. The ATCC number of the deposit is PTA-11715. The seed was tested on Mar. 15, 2011 and found viable. Access to this deposit will be available during the pendency of the application to the Commissioner for patents and persons determined by the Commissioner to be entitled thereto upon request. Upon granting of a patent on any claims in the application, the Applicants will make the deposit available to the public pursuant to 37 CFR §1.808. Additionally, Applicants will meet the requirements of 37 CFR §1.801-1.809, including providing an indication of the viability of the sample when the deposit is made. The ATCC deposit will be maintained in that depository, which is a public depository, for a period of 30 years, or 5 years after the last request, or for the enforceable life of the patent, whichever is longer, and will be replaced if it becomes nonviable during that period.

Accordingly, the present invention has been described with some degree of particularity directed to the preferred embodiment of the present invention. It should be appreciated, though that the present invention is defined by the following claims construed in light of the prior art so that modifications or changes may be made to the preferred embodiment of the present invention without departing from the inventive concepts contained herein.

What is claimed is:

1. A seed of soybean cultivar S07-02JR409106, representative seed of said soybean cultivar S07-02JR409106 having been deposited under ATCC Accession Number PTA-11715.

2. A soybean cultivar S07-02JR409106, representative seed of said soybean cultivar S07-02JR409106 having been deposited under ATCC Accession Number PTA-11715.

3. A plant part of the plant of claim 2.

4. The plant part of claim 3, wherein said part is pollen, or an ovule.

5. A soybean plant, or a part thereof, comprising all the physiological and morphological characteristics of the soybean cultivar S07-02JR409106, representative seed of said soybean cultivar having been deposited under ATCC Accession Number PTA-11715.

6. A tissue culture of cells or protoplasts from the plant, or part thereof, of claim 2.

7. A soybean plant regenerated from the tissue culture of claim 6, wherein said tissue culture comprises regenerable cells or protoplasts, said regenerated soybean plant expresses all of the physiological and morphological characteristics of the soybean cultivar S07-02JR409106.

8. A method for producing a soybean seed comprising crossing soybean plants and harvesting the resultant soybean seed, wherein at least one soybean plant is the soybean plant of claim 2.

9. A method for producing hybrid soybean seed comprising crossing the soybean plant according to claim 2 with a second different soybean plant and harvesting the resultant hybrid soybean seed.

10. An F.sub.1 hybrid seed produced by the method of claim 9.

11. A method for producing a cultivar S07-02JR409106 derived soybean plant, comprising: a) crossing soybean cultivar S07-02JR409106 according to claim 2, a sample of said soybean cultivar seed deposited under ATCC Accession Number PTA-11715, with a second soybean plant to yield progeny soybean seed; and b) growing said progeny soybean seed to yield said S07-02JR409106-derived soybean; (c) crossing the S07-02JR409106-derived soybean with itself or a second plant to produce a seed of a progeny plant of a subsequent generation; (d) growing a progeny plant of a subsequent generation from said seed and crossing the progeny plant of a subsequent generation with itself or a second plant; and (e) repeating steps (c) and (d) for an addition 0-10 generations with sufficient inbreeding to produce a cultivar S07-02JR409106-derived soybean.

12. A method of producing a plant of soybean cultivar S07-02JR409106 comprising an added desired trait, the method comprising introducing at least one transgene or locus conferring the desired trait into a plant of soybean cultivar S07-02JR409106 according to claim 2.

13. The method of claim 12, wherein the desired trait is selected from the group consisting of male sterility, herbicide tolerance, insect or pest resistance, disease resistance, fungal resistance, modified fatty acid metabolism, and modified carbohydrate metabolism.

14. The method of claim 13, wherein the desired trait is herbicide tolerance and the tolerance is conferred to an herbicide selected from the group consisting of glyphosate, sulfonylurea, imidazalinone, dicamba, glufosinate, phenoxy proprionic acid, cycloshexone, triazine, benzonitrile and broxynil.

15. The method of claim 12, wherein the desired trait is insect resistance and the transgene encodes a *Bacillus thuringiensis* (Bt) endotoxin.

16. A plant produced by the method of claim 12, wherein the plant comprises the desired trait and otherwise comprises all of the physiological and morphological characteristics of soybean cultivar when grown in the same location and in the same environmental conditions.

17. A method of producing a progeny soybean cultivar derived from S07-02JR409106 comprising a desired trait wherein the method comprises: (a) crossing a S07-02JR409106 plant, of claim 2 with a plant of another soybean cultivar that comprises a desired trait to produce F1 progeny plants, wherein the desired trait is selected from the group consisting of male sterility, herbicide resistance, insect resistance, modified fatty acid metabolism, modified carbohydrate metabolism and resistance to bacterial disease, fungal disease or viral disease; (b) selecting one or more F1 progeny plants that have the desired trait to produce selected progeny plants; (c) crossing the selected progeny plants with the S07-02JR409106 plants to produce backcross progeny plants; (d) selecting for backcross progeny plants that have the desired trait and physiological and morphological characteristics of soybean cultivar S07-02JR409106 to produce selected backcross progeny plants; and (e) repeating steps (c) and (d) three or more times in succession to produce selected fourth or higher backcross progeny plants that comprise the desired trait and all of the physiological and morphological characteristics of soybean cultivar S07-02JR409106 when grown in the same location and in the same environment.

18. A plant produced by the method of claim 17, wherein the plant has the desired trait and all of the other physiological and morphological characteristics of soybean cultivar S07-02JR409106 when grown in the same location with the same environmental conditions.

19. A method of producing a commodity plant product, comprising obtaining the plant of claim 2 or a part thereof and producing said commodity plant product comprising protein concentrate, protein isolate, soybean hulls, meal, flour or oil therefrom.

20. A method of producing a treated seed of claim 1 comprising obtaining the seed claim 1 and treating said seed.

* * * * *